US012265210B2

(12) United States Patent
Kolster et al.

(10) Patent No.: US 12,265,210 B2
(45) Date of Patent: Apr. 1, 2025

(54) OPERATING MICROSCOPE HAVING AN ILLUMINATION DEVICE

(71) Applicant: Carl Zeiss Meditec AG, Jena (DE)

(72) Inventors: Daniel Kolster, Oberkochen (DE); Manuel Steidle, Aalen (DE); Peter Reimer, Ellwangen (DE); André Mueller, Koenigsbronn-Zang (DE); Franz Merz, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/244,249

(22) Filed: Sep. 9, 2023

(65) Prior Publication Data

US 2023/0418036 A1    Dec. 28, 2023

Related U.S. Application Data

(63) Continuation of application No. PCT/EP2022/055773, filed on Mar. 7, 2022.

(30) Foreign Application Priority Data

Mar. 12, 2021 (DE) ...................... 10 2021 106 064.8

(51) Int. Cl.
*G02B 21/06* (2006.01)
*G02B 21/00* (2006.01)
(Continued)

(52) U.S. Cl.
CPC ......... *G02B 21/0012* (2013.01); *G02B 21/06* (2013.01); *G02B 21/086* (2013.01); *G02B 21/361* (2013.01)

(58) Field of Classification Search
CPC .......................... G02B 21/00; G02B 21/0004; G02B 21/0012; G02B 21/0016; G02B 21/0028;
(Continued)

(56) References Cited

U.S. PATENT DOCUMENTS

| 6,011,647 A | 1/2000 | Geschwentner |
| 7,307,785 B2 | 12/2007 | Obrebski et al. |

(Continued)

FOREIGN PATENT DOCUMENTS

| DE | 4344770 A1 | 6/1995 |
| DE | 10304267 A1 | 8/2004 |

(Continued)

OTHER PUBLICATIONS

International Preliminary Report on Patentability dated Feb. 21, 2023, in international application PCT/EP2022/055773 (on which this application is based) and English language translation thereof.
(Continued)

*Primary Examiner* — Thong Q Nguyen
(74) *Attorney, Agent, or Firm* — Ewers IP Law PLLC; Falk Ewers

(57) ABSTRACT

A surgical microscope includes an optical assembly to image an object plane with a microscope main objective system, through which a first stereoscopic partial beam path with a first optical axis and a second stereoscopic partial beam path with a second optical axis pass. An illumination device includes a light source assembly to provide illumination light in a luminous plane, with a radiant field stop, and an illumination optical unit which at least partially images a luminous object arranged in the luminous plane in the illumination beam path into a luminous image plane located in the microscope main objective system or for the vertical distance z of which from the microscope main objective system on the side facing the object region or the side facing away from the object region, in relation to a focal length f of the microscope main objective system, the following applies: $z/f<10\%$.

19 Claims, 7 Drawing Sheets

(51) Int. Cl.
*G02B 21/08* (2006.01)
*G02B 21/36* (2006.01)

(58) Field of Classification Search
CPC .. G02B 21/0032; G02B 21/006; G02B 21/02; G02B 21/025; G02B 21/06; G02B 21/084; G02B 21/10; G02B 21/12; G02B 21/125; G02B 21/22
USPC .................................................. 359/368–398
See application file for complete search history.

(56) References Cited

U.S. PATENT DOCUMENTS

| | | |
|---|---|---|
| 7,907,336 B2 | 3/2011 | Abele et al. |
| 8,159,743 B2 | 4/2012 | Abele et al. |
| 8,708,493 B2 * | 4/2014 | Reimer ................. A61B 90/30 351/205 |

FOREIGN PATENT DOCUMENTS

| | | |
|---|---|---|
| DE | 102007041003 A1 | 12/2008 |
| DE | 102009036913 A1 | 2/2011 |
| JP | H09105866 A | 4/1997 |
| WO | 2006015690 A1 | 2/2006 |
| WO | 2012150613 A2 | 11/2012 |

OTHER PUBLICATIONS

Office Action issued in German Patent Application No. DE 10 2021 106 064.8, dated Nov. 5, 2021, (from which this application claims priority) and English language translation thereof.

* cited by examiner

OPERATING MICROSCOPE HAVING AN ILLUMINATION DEVICE

CROSS REFERENCE TO RELATED APPLICATIONS

This application is a continuation application of international patent application PCT/EP2022/055773, filed Mar. 7, 2022, designating the United States and claiming priority to German application 10 2021 106 064.8, filed Mar. 12, 2021, and the entire content of both applications is incorporated herein by reference.

TECHNICAL FIELD

The disclosure relates to a surgical microscope having an optical assembly configured to image an object plane, which is arranged in an object region, into an image plane, the optical assembly containing a microscope main objective system, through which a first stereoscopic partial beam path with a first optical axis and a second stereoscopic partial beam path with a second optical axis pass, and having an illumination device for illuminating the object region with an illumination beam path, said illumination device containing a light source assembly for providing illumination light in a luminous plane, having a radiant field stop arranged at a distance from the luminous plane, and including an illumination optical unit configured to image the radiant field stop in a radiant field stop plane on a side of the microscope main objective system facing the object region with a beam path passing through the microscope main objective system.

BACKGROUND

A surgical microscope of the type set forth at the outset is known from DE 10 2007 041 003 A1. This surgical microscope is an ophthalmic surgical microscope. For the purpose of illuminating the object region, said surgical microscope contains an illumination device which enables setting of an illumination beam path that runs coaxially with the stereoscopic observation beam paths in the surgical microscope and passes through the microscope main objective system in the process. The illumination device includes a double stop which acts as an aperture stop and is arranged in the illumination beam path. This double stop is imaged via an illumination optical unit and the microscope main objective system into a stop plane which is at infinity or which is arranged far away from the microscope main objective system on a side of the microscope main objective system facing the object region. The illumination beam path emerging from the microscope main objective system consequently is parallel or slightly convergent on the exit side of the microscope main objective system. In the surgical microscope, however, the image of the double stop can also be arranged far away from the microscope main objective system on a side of the microscope main objective system facing away from the object region. In this case, the image of the double stop is virtual, and the illumination beam path is slightly divergent on the exit side of the microscope main objective system. The illumination beam path imaging the double stop depends on the focal length of the microscope main objective system and guides the illumination light into the object region in such a way that said light is incident there at a single angle with respect to the optical axes of the stereoscopic partial observation beam paths or at angles with respect to the optical axes of the stereoscopic partial observation beam paths that are in a narrow angular range.

WO 2012/150613 A2 describes a stereo surgical microscope having an illumination device in which illumination light for illuminating the object region, in which the patient's eye is arranged, is provided with a luminous object embodied as a light emitting diode (LED). The illumination device contains a condenser lens system and a relay lens system, a beam splitter prism with mirror surfaces, and a mirror arrangement with a first deflection mirror and a second deflection mirror, arranged on the side of the microscope main objective system facing away from the object region. The condenser lens system and the relay lens system image the LED onto a mirror surface of the mirror arrangement via the beam splitter prism. Thus, a virtual luminous area is generated there, and it is arranged in or near at least one of the stereoscopic partial observation beam paths. The light from the virtual luminous area can therefore cause a red reflex on the fundus of the patient's eye, and this is observable in the stereoscopic partial observation beam path.

WO 2006/015690 A1 describes a surgical microscope having an adjustable illumination device which, in a first setting, enables the provision of red reflex illumination light in the object region and which, in a second setting different therefrom, is able to provide illumination light for the ambient illumination of the object region in the object region. For the provision of red reflex illumination light, an intermediate image of the end of a light guide generated with the collector in the plane of an illumination light aperture stop is imaged at infinity with a collector via a plano-convex lens, a relay lens system and the microscope main objective system, with the result that an image of the end of the light guide is formed on the fundus of an emmetropic patient's eye.

DE 10 2009 036 913 A1 describes a surgical microscope having an adjustable illumination device, in which illumination light for illuminating the object plane is provided with a luminous object in the form of a light guide. With illumination mirrors, it is possible to guide the illumination light to the object region through the microscope main objective on four different light paths:

In a first setting, the illumination light from the light guide is firstly used to illuminate a radiant field stop, which is imaged via a collector optical system and the microscope main objective into the object plane in an illumination beam path.

Secondly, the illumination light from the light guide in this setting illuminates a radiant field stop arranged at a distance from the light exit plane, said radiant field stop then being imaged into the object plane through an illumination op-tical unit in the form of a condenser optical system and the microscope main objective. In this case, the light from the light guide provided in the light exit plane is guided with a collector optical system to an aperture stop which images the condenser optical system and the microscope main objective to infinity.

In two further different settings of the described illumination device, the illumination light from the light guide can be guided in a folded beam path through the condenser optical system and the microscope main objective to the object region in order to generate the image of a slit aperture there.

DE 103 04 267 A describes an eye surgery microscopy system having an illumination device with a white light source. The illumination device provides the illumination light with a beam path which is guided through a collimation optical unit, and which contains background illumination beams in order to cause a red reflex in the patient's eye, and additionally has normal illumination beams which serve to illuminate the object plane with normal light.

DE 43 44 770 A1 describes an illumination device for a surgical microscope, in which the light from a light source is guided in the illumination beam path through a microscope main objective into an object plane with a patient's eye via an optical system having a collector lens system, a radiant field stop, a deflection prism and a further lens.

JP H09 105866 A describes a surgical microscope in which the brightness of the red reflex can be adjusted in order thereby to protect the retina against illumination that is too bright. In this case, the illumination light is provided from a light guide at a light exit surface, is guided through a converging lens and is steered through the microscope main objective to the object region with a prism and a parallelogram prism with mirror surfaces. The amount of light guided into the object region can be adapted in the surgical microscope by adjusting a stop located in the beam path for the illumination light between the prism and the parallelogram prism.

SUMMARY

It is an object of the disclosure to provide a surgical microscope having an illumination device for illuminating the object region with an illumination beam path, which guides the illumination light into the object region at different angles, from within a wide angular range, with respect to the optical axes of stereoscopic partial observation beam paths.

The object is achieved by the surgical microscope as described herein.

A surgical microscope according to an aspect of the disclosure has an optical assembly configured to image an object plane, which is arranged in an object region, into an image plane. The optical assembly contains a microscope main objective system, through which a first stereoscopic partial beam path with a first optical axis and a second stereoscopic partial beam path with a second optical axis pass. In the surgical microscope, there is an illumination device for illuminating the object region with an illumination beam path, said illumination device containing a light source assembly for providing illumination light in a luminous plane, having a radiant field stop arranged at a distance from the luminous plane, and including an illumination optical unit configured to image the radiant field stop in a radiant field stop plane on a side of the microscope main objective system facing the object region with a beam path passing through the microscope main objective system. In the surgical microscope, the illumination optical unit at least partially images a luminous object arranged in the luminous plane in the illumination beam path into at least one luminous image plane which is located in the microscope main objective system or for the vertical distance z of which from the microscope main objective system on the side facing the object region or the side facing away from the object region, in relation to a focal length f of the microscope main objective system, the following applies: $z/f \leq 10\%$, typically $z/f \leq 5\%$, particularly typically $z/f \leq 2.5\%$.

The luminous image plane can be perpendicular to the optical axis of the microscope main objective system.

An idea of the disclosure is that the object region of a surgical microscope can be illuminated with light which reaches the object region at different angles, which lie in a defined angular range, with respect to the optical axes of the stereoscopic partial beam paths when this illumination light is provided at light exit surfaces arranged in the microscope main objective system or just there above or there below. One concept of the disclosure is that the angular range can be defined by the geometric shape and size of the luminous areas and the position and orientation thereof in relation to the optical axes of the stereoscopic partial beam paths.

It is advantageous if the illumination optical unit images a luminous object arranged in the luminous plane with magnification. In this way, illuminating comparatively small luminous areas in the luminous plane makes it possible to provide illumination light which is incident on the object region with angles of incidence that lie in a large angular range.

Typically, the light source assembly is configured to provide illumination light with an extensive luminous pattern in the luminous plane, the illumination optical unit imaging said luminous pattern as a luminous pattern image into the at least one sectional plane optically conjugate to the luminous plane.

BRIEF DESCRIPTION OF THE DRAWINGS

The disclosure will now be described with reference to the drawings wherein.

DESCRIPTION OF EXEMPLARY EMBODIMENTS

Figure 1:
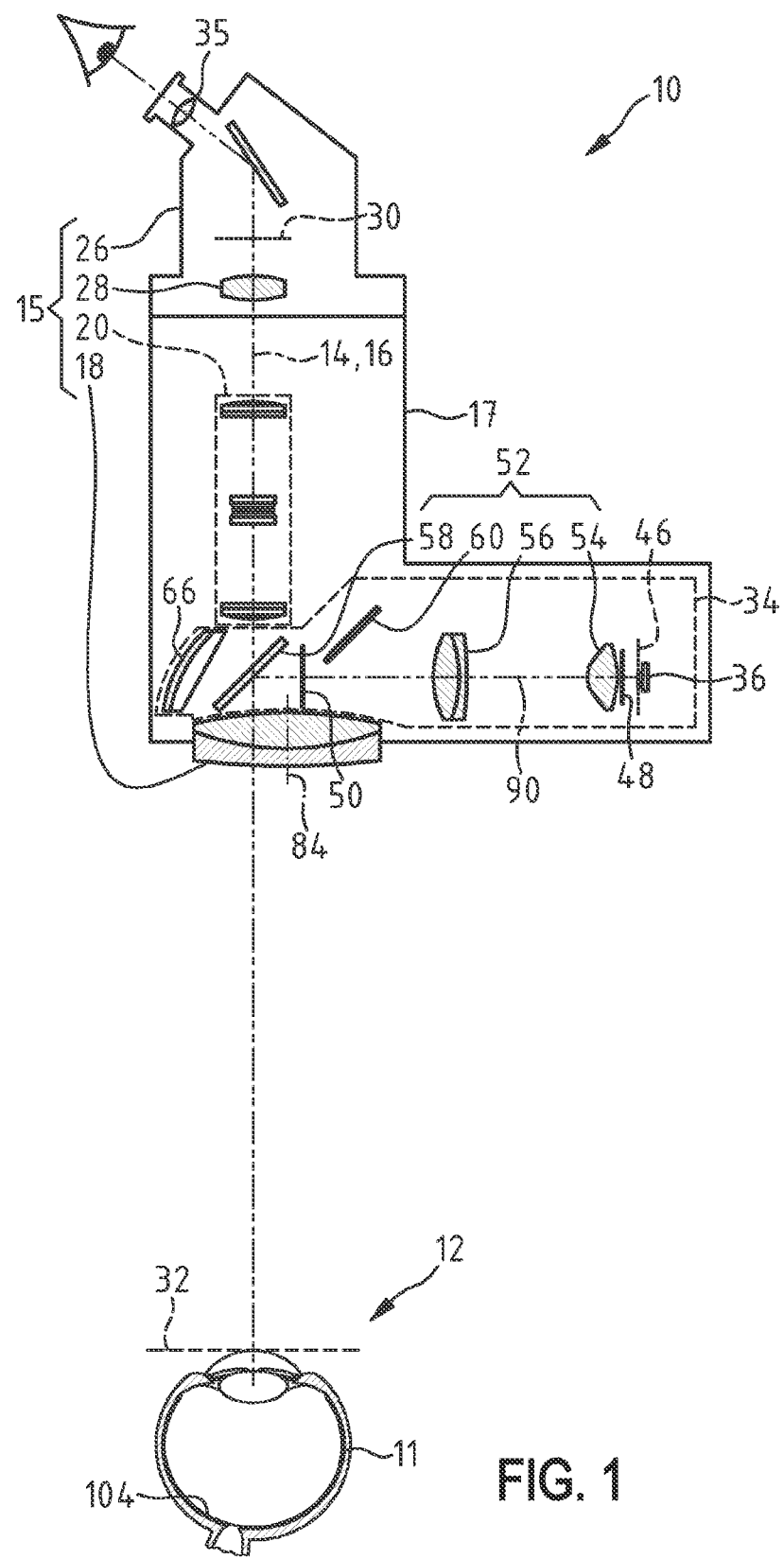
FIG. 1 shows a surgical microscope embodied as an ophthalmic surgical microscope for visualizing an object region using a microscope main objective system and using an illumination device.

With reference to FIG. 1, in cataract operations, which are generally performed under a surgical microscope 10, there is a need to image transparent structures in an anterior eye segment of a patient's eye 11 with high contrast. This requires what is known as red reflex illumination, in which the pupil of the patient's eye 11 is illuminated using light reflected and/or backscattered at the eye's retina.

The inventors have recognized that transparent structures in the anterior eye segment of a patient's eye 11 can be made clearly visible especially if the light reflected and/or backscattered at the retina illuminates the pupil of the patient's eye homogeneously and brightly and if this light is substantially caused by parts of the retina that correspond to the region through which pencils of the rays of the stereoscopic partial observation beams pass, whereby a phase contrast is created.

One concept of the disclosure is therefore to configure the light source assembly 36 to provide illumination light with an extensive luminous pattern in the luminous plane 46, which causes a luminous pattern image that is largely guided in the stereoscopic partial observation beam paths 78, 80.

By virtue of the luminous pattern image being located at least in part on a straight line that perpendicularly intersects the optical axis 14 of the first stereoscopic partial observation beam path and the optical axis 16 of the second stereoscopic partial observation beam path in this sectional plane, it is possible to provide illumination light which is incident on the object region near the axis with respect to the stereoscopic partial observation beam paths 78, 80.

Alternatively or in addition, it is also possible for the first stereoscopic partial observation beam path to at least partially pass through the luminous pattern image and/or the second stereoscopic partial observation beam path to at least partially pass through the luminous pattern image. In this way, it is possible to guide illumination light to the object region 12, said illumination light being incident on object region 12 in the stereoscopic partial observation beam paths.

It should be observed that the optical axis 14 of the first stereoscopic partial observation beam path can alternatively or additionally pass through the luminous pattern image and/or the optical axis 16 of the second stereoscopic partial observation beam path can pass through the luminous pattern image. In this way, illumination light coaxial with an optical axis of the stereoscopic partial observation beam path is guided to the object region.

It is a further concept of the disclosure to provide the illumination light of an extensive luminous pattern imaged into a luminous image plane 65 located in the microscope main objective system 18 or arranged at an only small distance therefrom being guided into the object region using light rays that diverge and cover the entire field of view of the surgical microscope, even at the lowest possible magnification. What is possible to achieve by virtue of the dimensions of the luminous image pattern being small in comparison with the diameter of the microscope main objective system is that, even with a working distance of the object region in a range from 175 mm to 200 mm or else slightly there above or slightly there below, the illumination light is incident on the object region in directed fashion at angles with respect to the optical axes of the stereoscopic partial observation beam paths, said angles being in an angular range that emerges from the position of the luminous image pattern.

It is advantageous if the light source assembly is c to set one extensive luminous pattern or a plurality of extensive luminous patterns from the following group:
a single luminous area;
a first luminous area and a second luminous area arranged at a distance from the first luminous area, the first luminous area and the second luminous area being mirror-symmetrical in relation to an optical axis of the illumination optical unit;
a first luminous area, a second luminous area and a third luminous area whose centroids in the luminous plane define a triangle, typically an isosceles triangle, in particular a right-angled triangle, with a height h perpendicularly intersecting the base c, the illumination optical unit imaging the base c of this triangle onto a straight line perpendicularly intersecting the optical axis of the first stereoscopic partial observation beam path and the optical axis of the second stereoscopic partial observation beam path in the luminous image plane in such a way that the image of the point of intersection of the height h with the base c of the triangle is located on the centre point of the distance line perpendicularly intersecting the optical axis of the first stereoscopic partial observation beam path and of the second stereoscopic partial observation beam path in the luminous image plane.

In particular, the light source assembly can be configured to set different luminous patterns. For example, the luminous pattern can have at least a rectangular luminous area or a square luminous area. However, the luminous pattern can also have one or more round, in particular circular or oval, luminous areas. It should be observed that the luminous pattern can in principle have any shape that ensures that as much illumination light as possible reaches a luminous field on the object region without disturbing reflections of illumination light occurring in the observation beam paths. Typically, the illumination optical unit 52 in a surgical microscope according to an aspect of the disclosure includes a deflection element 58 which is arranged on the side of the microscope main objective system facing away from the object region, which serves to deflect illumination light provided with the illumination device to the object region, and which has a mirror surface which is parallel to the stereo base of the first stereoscopic partial beam path and the second stereoscopic partial beam path and in which a straight line coaxial with the stereo base runs.

The deflection element 58 can be configured, for example, as a beam splitter through which the first stereoscopic partial beam path 78 and the second stereoscopic partial beam path 80 pass. The illumination device 34 can have a mirror element which is arranged on the side of the microscope main objective system facing away from the object region, which is positioned at a distance from the optical axis of the microscope main objective system, and which, for the deflection of illumination light to the object region, has a mirror surface parallel to the stereo base of the first stereoscopic partial beam path and the second stereoscopic partial beam path.

In order to avoid disturbing light reflections caused by illumination light from the illumination beam path from occurring in the first and/or in the second stereoscopic partial observation beam path, it is advantageous if a reflection stop 50 serving to suppress illumination light reflections in the first and/or second stereoscopic partial beam path on a side of an optically effective surface of the microscope main objective system facing away from the object region is arranged in the illumination beam path on the side of the microscope main objective system facing away from the object region, positioned at a distance both from the luminous plane and from the at least one luminous image plane optically conjugate thereto.

This reflection stop 50 is typically arranged in a stop plane parallel to the optical axes of the first stereoscopic partial observation beam path and the second stereoscopic partial observation beam path.

The reflection stop 50 can have a mirror-symmetrical stop structure and can, for example, include five light passage surfaces separated from one another by opaque regions. It should be observed that the light passage surface of the reflection stop 50 can in principle also have a single contiguous shape, which can for example be produced by vapor deposition of opaque material on a glass substrate. In particular, the reflection stop 50 can be arranged in a portion of the illumination beam path in which the latter is convergent or is divergent.

As an alternative or in addition to the reflection stop 50, the occurrence of disturbing light reflections in the first and/or in the second stereoscopic partial observation beam path can also be counteracted by virtue of the luminous pattern generated by the light source assembly bringing about a luminous image pattern in the luminous image plane, said luminous image pattern suppressing or at least minimizing the disturbing light reflections that the illumination light can cause on the microscope main objective system by reflections.

It should be observed that the reflection stop 50 can be configured as a transmissive display in particular. Moreover, it should be observed that the light source assembly for generating luminous patterns may contain a reflective display (DMD), for example.

It should also be observed that the arrangement of the luminous areas of the light sources of the light source assembly can be optimized in principle in order to avoid disturbing reflections of illumination light at the microscope main objective system 18 into the stereoscopic partial observation beam paths. Alternatively or in addition, it is possible to adapt radii of optically effective surfaces of the microscope main objective system which determine the direction of the reflected illumination light and thus also the reflection light detected by the observation. Moreover, an off-centered position of the stereoscopic partial observation beam paths and of the illumination beam path in relation to the optical axis of the microscope main objective system makes it possible to suppress or reduce disturbing reflections of illumination light at the microscope main objective system into the stereoscopic partial observation beam paths.

Configured to image the luminous plane, the illumination device 34 can include a collector lens system 54 with an optical axis and can contain a converging lens system, the radiant field stop 48 being arranged between the luminous plane 46 and the collector lens system 54.

It should be observed that the light source assembly can include two light sources, each with an in particular round or else rectangular, for example square, luminous area, arranged in the luminous plane, said luminous areas having centroids which are spaced apart from one another and located on a straight line which perpendicularly intersects the optical axis of the collector lens system, the boundary sides of the luminous areas of the light sources each running obliquely or orthogonally with respect to this straight line.

The light source assembly 36 can include a light source with a rectangular or round luminous area which is arranged in the luminous plane and which has a centroid which is arranged at a distance from the optical axis of the collector lens system, the centroid being located on a straight line which perpendicularly intersects this optical axis and which is parallel to the luminous image plane optically conjugate to the luminous plane or to the optical axis of the microscope main objective system.

The light source assembly 36 can include, in particular, a light source with an in particular round or else rectangular, for example square, luminous area which is arranged in the luminous plane and which has a centroid which is arranged at a distance from the optical axis of the collector lens system and in the process is located on a straight line which perpendicularly intersects this optical axis and the luminous image plane conjugate to the luminous plane and which is parallel to the optical axis of the microscope main objective system.

It should be observed that the illumination optical unit 52 of the illumination device 34 in the surgical microscope may be configured such that a luminous object arranged in luminous plane 46 in the illumination beam path 64 is imaged at least in part into different luminous image planes, which are each located in the microscope main objective system or for the vertical distance z of which from the microscope main objective system on the side facing the object region or the side facing away from the object region, in relation to a focal length f of the microscope main objective system, the following applies: $z/f \leq 10\%$.

Provision can be made for the microscope main objective system 18 to have a plurality of sectional planes 62 which are optically conjugate to the luminous plane 46, and into which the illumination optical unit 52 at least partially images a luminous object arranged in the luminous plane 46.

Figure 2:
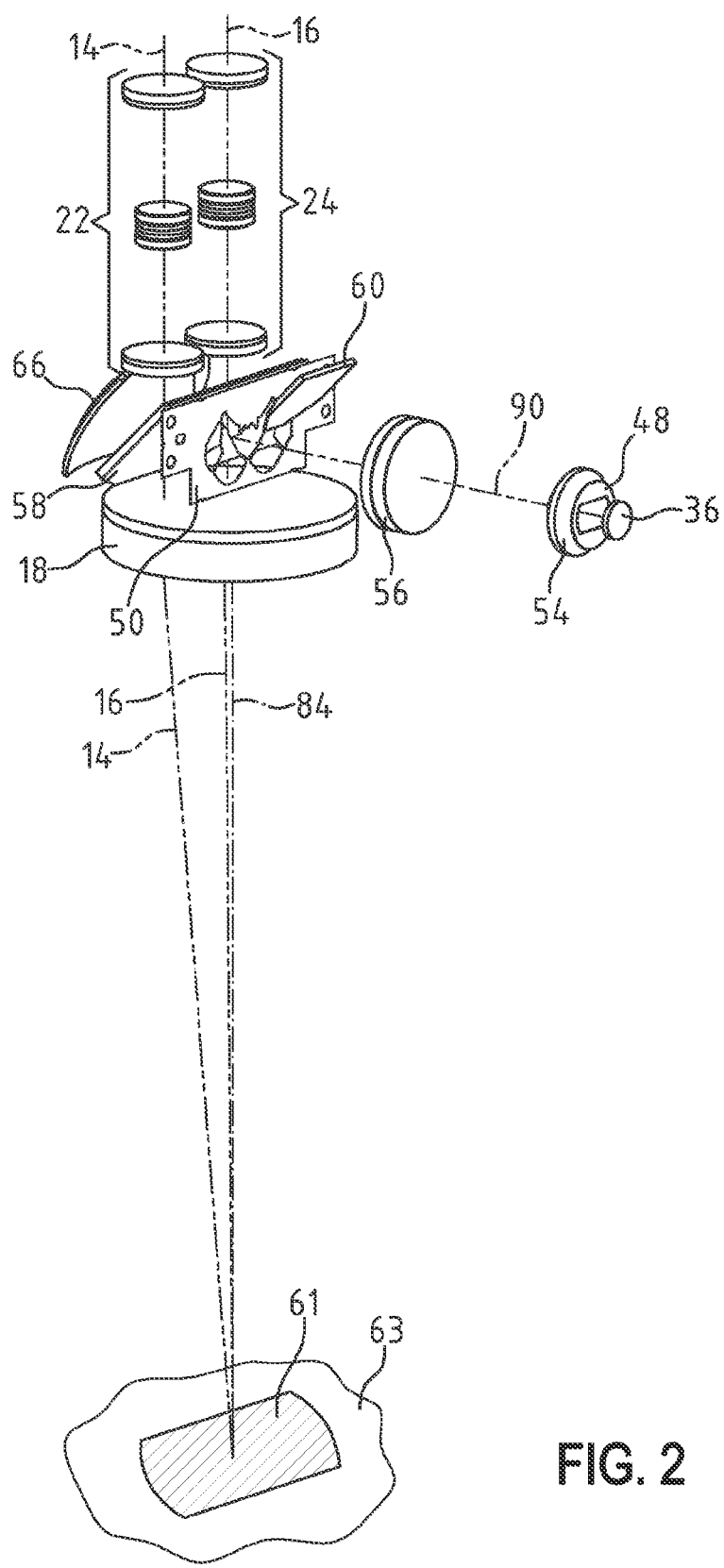
FIG. 2 and FIG. 3 show perspective partial views of the surgical microscope.
Figure 3:
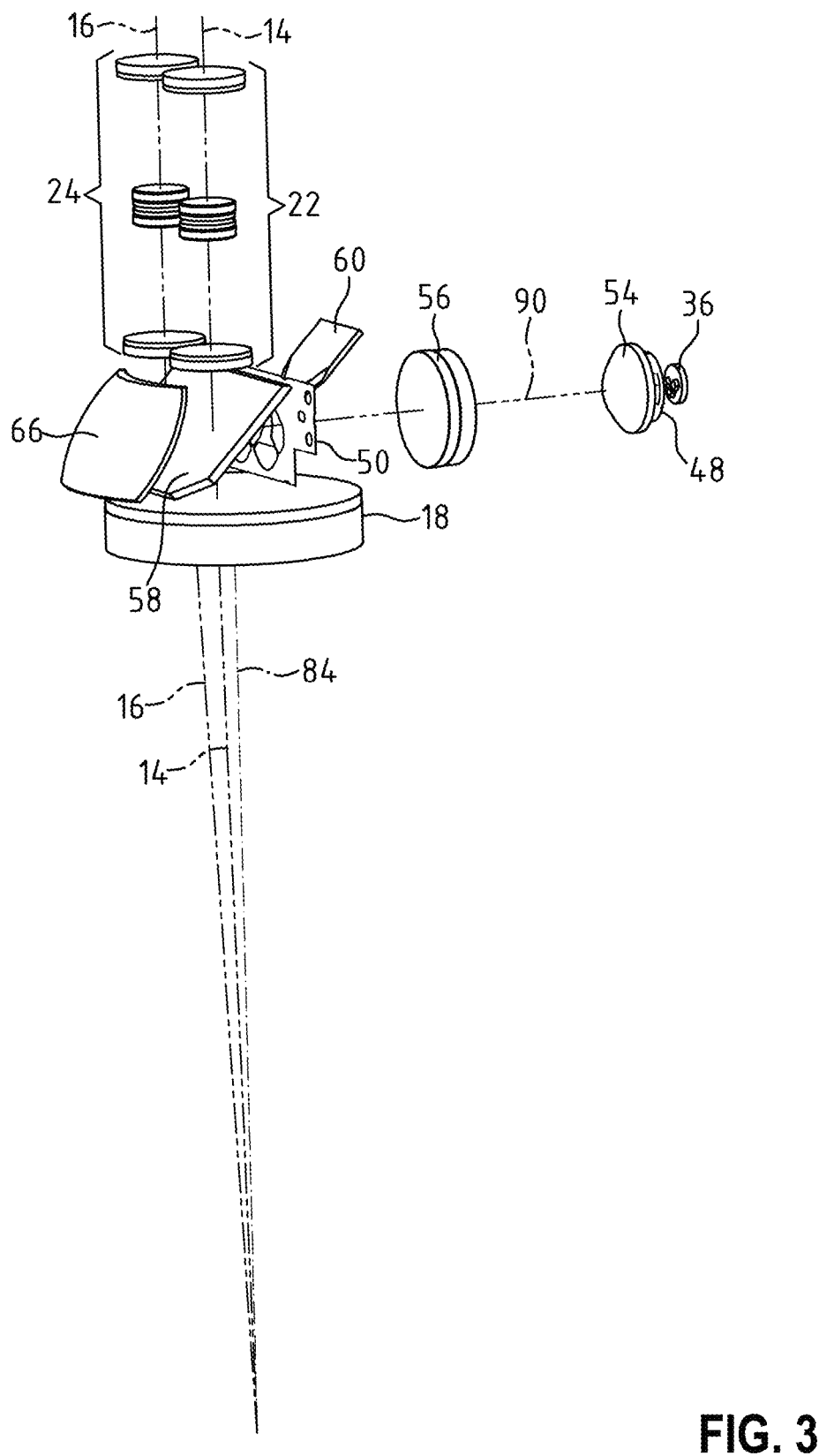

Referring back to FIG. 1, which is a schematic section through a surgical microscope 10 embodied as an ophthalmic surgical microscope. The surgical microscope 10 serves for visualizing a patient's eye 11 in an object region 12 during surgical operations using a first and second stereoscopic partial observation beam path. To this end, it contains an optical assembly 15 including a microscope main objective system 18 which is accommodated in a surgical microscope main body 17 and through which the stereoscopic partial observation beam paths with first and second optical axes 14, 16 pass. FIG. 2 and FIG. 3 show different perspective partial views of assemblies in the surgical microscope 10.

The optical assembly 15 in the surgical microscope 10 contains a pancratic magnification system 20 embodied as an afocal zoom system and having a first adjustable lens assembly 22 and having a second adjustable lens assembly 24. The optical assembly 15 in the surgical microscope 10 includes a binocular tube 26 with tube lenses 28, which generate the image of an object plane 32 in an image plane 30 in the first and second stereoscopic partial observation beam path with the optical axes 14 and 16, said image being able to be viewed through eyepiece lenses 35 with magnification by the eyes of an observer. It should be observed that a modified exemplary embodiment of the surgical microscope can include a binocular tube with image sensors for capturing the image in the image plane 30, in order hence to digitally capture the image of the object region 12 such that said image can be displayed to an observer, for example with displays. The surgical microscope 10 has an illumination device 34 with a light source assembly 36 for the purpose of providing illumination light in the object region 12.

Figure 4:
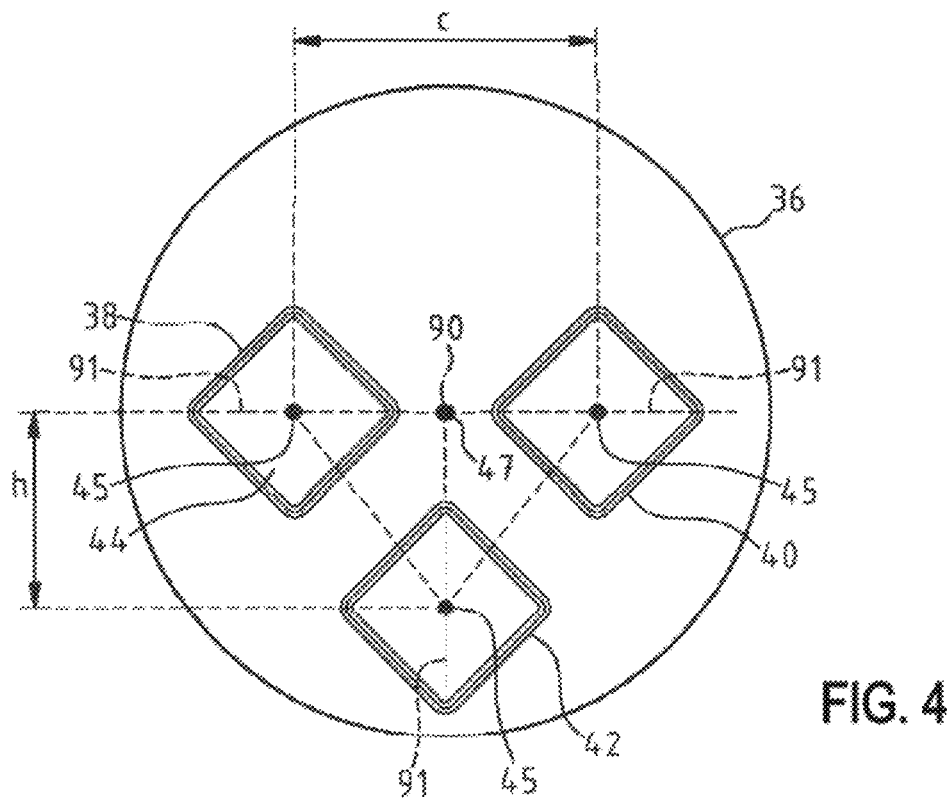
FIG. 4 shows a plan view of a light source assembly of the illumination device with light sources that have luminous areas located in a luminous plane.

FIG. 4 is a plan view of the light source assembly 36. The light source assembly 36 serves to provide an extensive luminous pattern in a luminous plane 46. To this end, it contains three light sources 38, 40, 42, which each have square luminous areas 44 arranged in the luminous plane 46.

The light sources 38, 40 serve to generate illumination light, which illuminates the object region 12 near the axis in relation to the optical axes 14, 16 of the stereoscopic partial observation beam paths in the surgical microscope 10. By contrast, the illumination light generated by the light source 42 illuminates the object region 12 with an illumination beam path whose optical axis includes an angle with the optical axes 14, 16 of the stereoscopic partial observation beam paths in the object region 12. The light sources 38, 40, 42 of the light source assembly 36 are white light LEDs, which can be controlled independently of one another for the purpose of setting different luminous patterns in the luminous plane 46. The light sources 38, 40, 42 of the light source assembly 36 can be embodied as organic light-emitting diodes (OLEDs) in particular. Thus, by switching the light sources 38, 40, 42 on and off accordingly, it is possible in the surgical microscope to illuminate the object region 12 under the surgical microscope 10 only with near-axis illumination light or only with axis-remote illumination light or both with near-axis and with axis-remote illumination light, in relation to the optical axes 14, 16 of the stereoscopic partial observation beam paths.

It should be observed that, in a modified exemplary embodiment, the light source assembly 36 can also include the ends of light guides as light sources, into which appropriate illumination light is coupled for the purpose of generating an extensive luminous pattern in the luminous plane, even illumination light that is generated with thermal emitters such as a mercury-vapor lamp or a halogen lamp, for example. Moreover, it should be observed that, in a further modified exemplary embodiment, the light source assembly 36 can include light sources which illuminate the luminous plane, with aperture stops with different stop geometries being arrangeable for setting different luminous patterns in the luminous plane.

In the illumination device 34, there is a radiant field stop 48 and a reflection stop 50. The illumination device 34 includes an illumination optical unit 52 with a collector lens system 54 and with a converging lens system 56 in the form of a cemented member. The illumination optical unit 52 contains a deflection element 58 configured as a splitter mirror, which is arranged on a side of the microscope main objective system 18 facing away from the object region 12 and which passes through the first and second stereoscopic partial observation beam path with the optical axes 14, 16. This deflection element 58 serves to deflect illumination light from the luminous plane 46 to the object region 12 with an illumination beam path that passes through the microscope main objective system 18 in the vicinity of the optical axes 14, 16 of the first and second stereoscopic partial observation beam path.

The illumination optical unit 52 includes a mirror element 60 which is arranged at a distance from the deflection element 58 and which serves to deflect illumination light with an illumination beam path which, on the side facing away from the object region 12 of the microscope main objective system 18, extends remotely from the axis of the optical axes 14, 16 of the first and second stereoscopic partial beam paths in comparison with the optical axis of the illumination light deflected with the first deflection element 58. For the purpose of generating a luminous field 61, the illumination optical unit 52 images the radiant field stop 48, in magnified fashion, into a luminous field plane 63 which coincides with the object plane 32. The magnification V of this imaging can be in the range 4≤V≤8, for example, and is typically V≈6. However, it should be observed that the luminous field plane 63 can also be offset to a certain extent from the object plane 32, although this has a blurred edge of the luminous field as a consequence.

Figure 5:
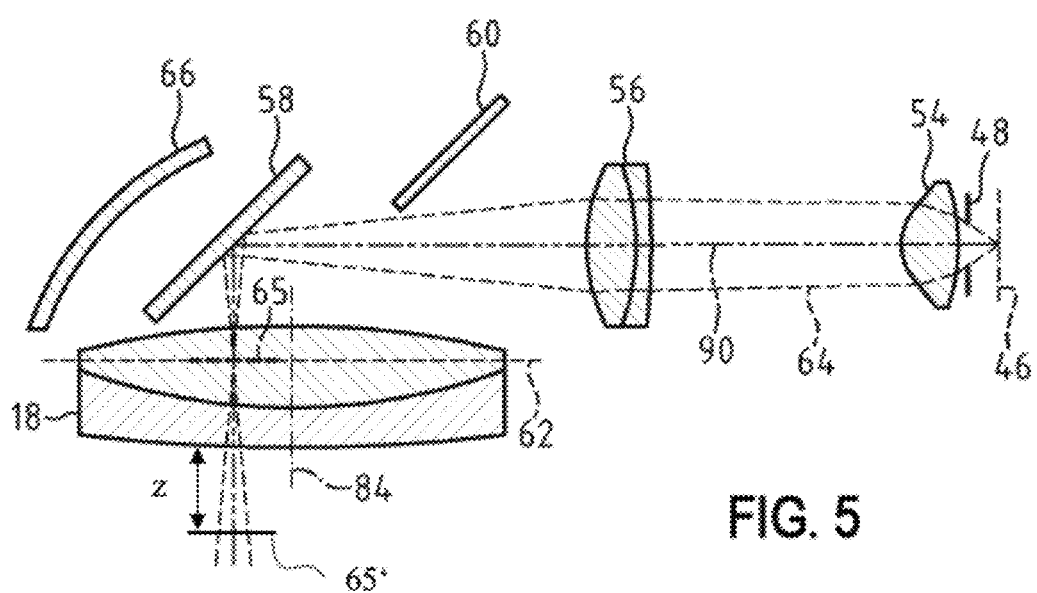
FIG. 5 shows a sectional view of the illumination device with a first beam path imaging the luminous plane into a sectional plane of the microscope main objective system.

FIG. 5 is a first partial section of the illumination device 34 with the microscope main objective system 18. The illumination optical unit 52 of the illumination device 34 causes magnified optical imaging of the luminous plane 46 into a luminous image plane 65 in the illumination beam path, said luminous image plane thus being optically conjugate to the luminous plane 46 and located in a sectional plane 62 of the microscope main objective system 18, with an illumination beam path 64 which is partly deflected into the microscope main objective system 18 with the deflection element 58, configured as a splitter mirror, on the side of the microscope main objective system 18 facing away from the object region 12 and which partly passes through the deflection element 58 to a light trap 66.

Figure 6:
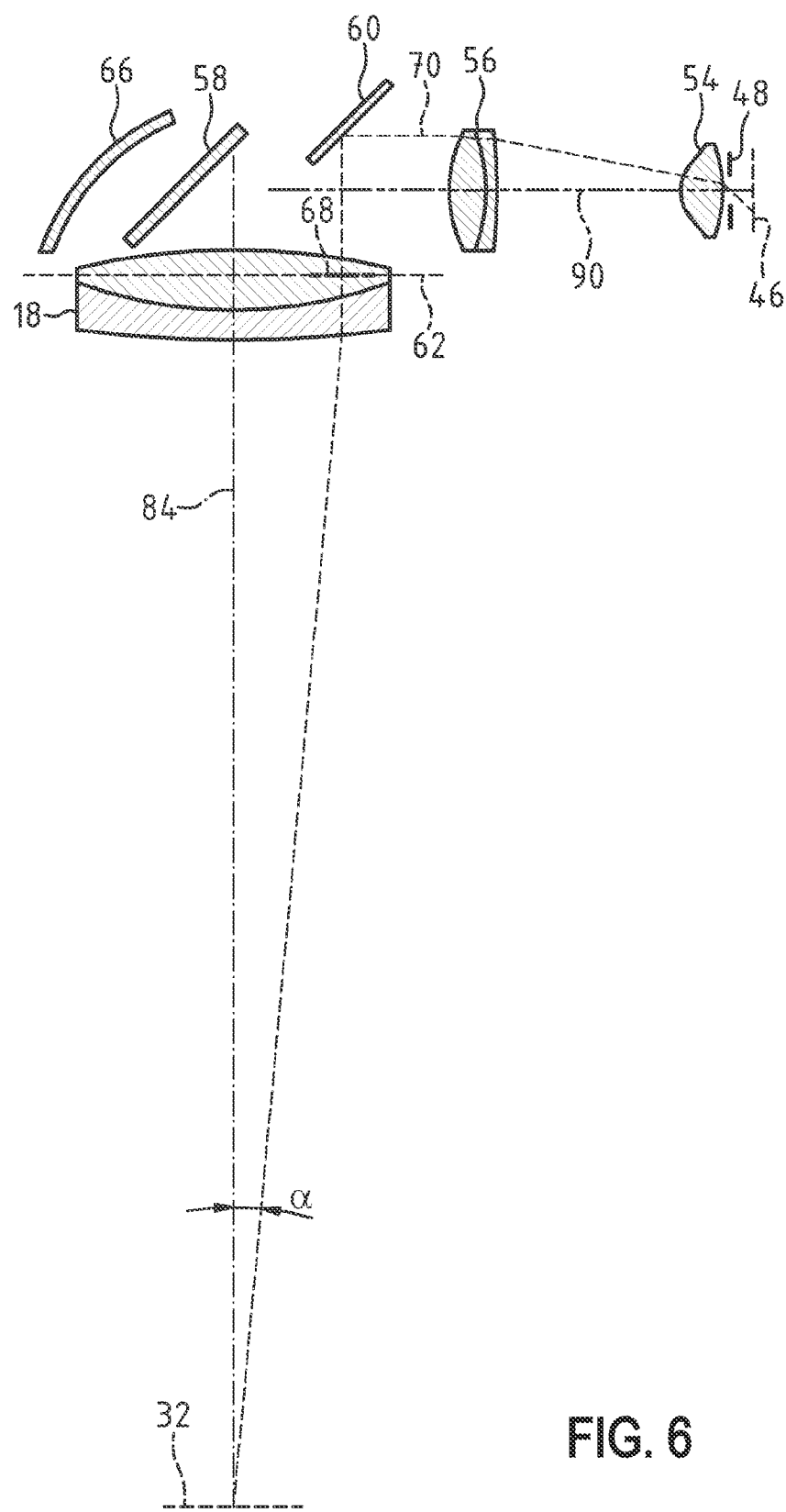
FIG. 6 shows a sectional view of the illumination device with a second beam path imaging the luminous plane into a sectional plane of the microscope main objective system.

A further partial section of the illumination device 34 with the microscope main objective system 18 can be seen in FIG. 6. The illumination optical unit 52 of the illumination device 34 also brings about optical imaging of the luminous plane 46 in a luminous image plane 68, which is thus likewise optically conjugate to the luminous plane 46 and located in a sectional plane 62 of the microscope main objective system 18, with a beam path which has an optical axis 70 and which is deflected into the microscope main objective system 18 with the mirror element 60. The optical axis 70 of the imaging beam path in this case intersects the optical axis 84 of the microscope main objective system 18 in the object plane 32 at the angle α≈5°.

In the surgical microscope 10, the luminous image planes 65, 68 of the illumination device 34 are located in sectional planes 62 which are somewhat apart from one another on account of different optical path lengths of the illumination beam path via, firstly, the deflection element 58 and, secondly, the mirror element 60. It should be observed, however, that the illumination device 34 can in principle also be configured such that the luminous image planes of the illumination device 34 are located in one and the same sectional plane of the microscope main objective system 18.

Moreover, it should be observed that, in a further modified exemplary embodiment of the surgical microscope, the luminous image planes can be located close to the microscope main objective system, for example at a vertical distance z from the microscope main objective system 18 on the side facing the object region 12 or the side facing away from the object region 12, said vertical distance, in relation to the focal length f of the microscope main objective system 18, being as follows: z/f≤10%. A luminous image plane 65' arranged at a vertical distance z from the microscope main objective system 18 on the side facing the object region 12 is shown in FIG. 5.

Figure 7:
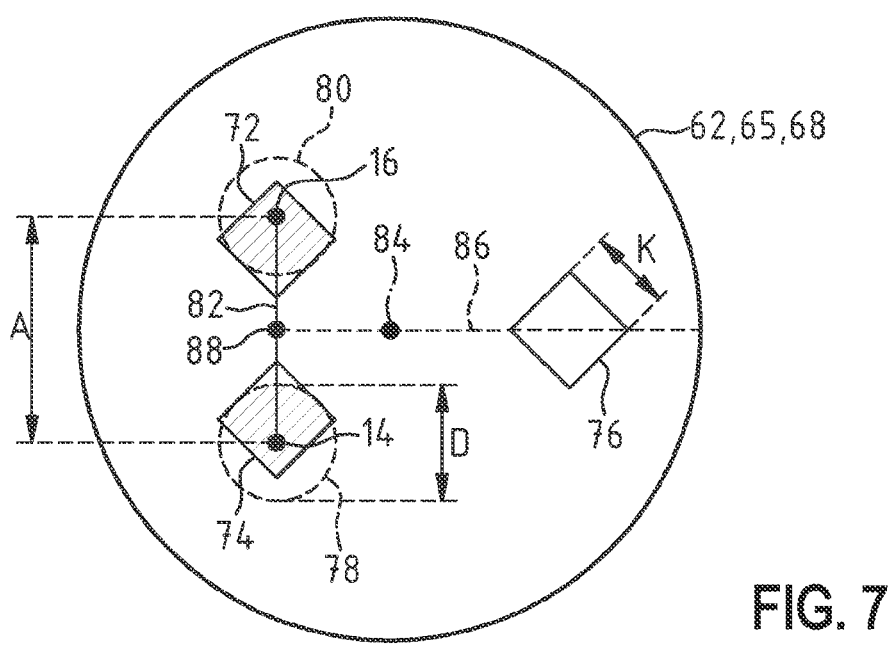
FIG. 7 shows a vertical projection onto sectional planes of the microscope main objective system with the pupils of the stereoscopic partial observation beam paths in the surgical microscope.

FIG. 7 is a vertical projection onto the sectional planes 62 of the microscope main objective system 18 with the images 72, 74, 76 of the luminous areas 44 of the light sources 38, 40, 42 in the light source assembly 36, the first and second stereoscopic partial observation beam paths 78, 80 with the optical axes 14, 16, and the stereo base 82 as the line connecting the points of intersection of the optical axes 14, 16 with the sectional planes 62.

In the surgical microscope 10, the first and second stereoscopic partial observation beam paths pass through the microscope main objective system 18 with optical axes 14, 16, the stereo base 82 of which is located away from the optical axis 84 of the microscope main objective system 18. The normal 86 dropped from the optical axis 84 of the microscope main objective system 18 onto the stereo base 82 intersects the stereo base at its center point 88.

The images 72, 74 of the luminous areas 44 of the light sources 38 and 40 in this case cover partial areas of the stereo base 82 which are arranged spaced apart from one another and in this case overlap with the first stereoscopic partial observation beam path 78 and the second stereoscopic partial observation beam path 80.

In the case of a diameter D of the stereoscopic partial observation beam paths of D≈16 mm, which depends on the setting of the magnification system 20 in the surgical microscope 10, and in the case of a distance A between the optical axes 14, 16 of the stereoscopic partial observation beam paths 78, 80 of A≈22 mm, the edge length K of the images 72, 74, 76 of the luminous areas of the light sources 38, 40 can be K≈10 mm, for example, with the back focal length of the main objective system being of the or-der of 200 mm, for example, and the diameter of the main objective system being approximately 60 mm.

In this case, the luminous pattern that can be generated in the luminous plane 46 with the light sources 38, 40, 42 when the light sources 38, 40, 42 are activated is consequently partly on a straight line which perpendicularly intersects the optical axis 14 of the first stereoscopic partial observation beam path and the optical axis 16 of the second stereoscopic partial observation beam path in the sectional plane 62, and which is coaxial to the stereo base 82 as the vertical connecting line of the optical axes 14, 16 in the sectional plane 62 of the microscope main objective system 18. The first stereoscopic partial observation beam path 78 partly passes through the luminous pattern image formed by the images 72, 74 and 76, specifically in the areas indicated by hatching in FIG. 7. The optical axis 14 of the first stereoscopic partial observation beam path 78 also passes through the luminous pattern image. The same applies to the optical axis 16 of the partial observation beam path 80.

By contrast, the image 76 of the luminous area 44 of the light source 42 in the sectional plane 62 of the microscope main objective system 18 covers the extension of the normal 86 which perpendicularly intersects the optical axis 84 of the microscope main objective system 18 and which emanates from the center point 88 of the stereo base 82. The distance of the image 76 of the luminous area 44 of the light source 42 from the stereo base 82 of the first and second stereoscopic partial observation beam path 78, 80 is slightly larger in this case than the distance of the stereo base 82 from the optical axis 84 of the microscope main objective system 18. It should be observed that this distance can, however, also correspond to the distance of the stereo base 82 from the optical axis 84 of the microscope main objective system 18 or be smaller than this distance.

The light source assembly 36 enables the setting of different extensive luminous patterns by virtue of the light sources 38, 40, 42 being controlled differently. For example, it is possible to generate luminous patterns with only a single square luminous area, which corresponds to the luminous areas 44 of the individual light sources 38, 40, 42. However, it is also possible to generate luminous patterns which include a luminous area 44 of a first of the light sources 38, 40, 42 and of a further one of the light sources 38, 40, 42. For example, it is thus possible to set a luminous pattern generated with the light sources 38 and 40, in the case of which the first luminous area and the second luminous area are mirror-symmetrical with respect to the optical axis 90 of the collector lens system 54 of the illumination optical unit 52. This luminous pattern for example causes a red reflex illumination for the patient's eye 11.

If all light sources 38, 40, 42 of the light source assembly 36 are activated, this creates a luminous pattern with a first luminous area, a second luminous area and a third luminous area with centroids 45 which, in the luminous plane 46, define an isosceles triangle with a height h perpendicularly intersecting the base c, the illumination optical unit imaging the base of this triangle onto a straight line perpendicularly intersecting the optical axis 14 of the first stereoscopic partial observation beam path 78 and the optical axis 16 of the second stereoscopic partial observation beam path 80 in the sectional plane 62 of the microscope main objective system 18 in such a way that the image of the point of intersection 47 of the height h with the base c of the triangle is located on the center point 88 of the distance line, corresponding to the stereo base 82, perpendicularly intersecting the optical axis 14 of the first stereoscopic partial observation beam path and the optical axis 16 of the second stereoscopic partial observation beam path in this sectional plane 62.

The luminous areas 44 of the light sources 38, 40, 42 are spaced apart from one another in order to avoid the illumination beam path 64 imaging the luminous areas 44 of the light sources 38, 40 in the sectional plane 62 of the microscope main objective system 18 being partially reflected into the stereoscopic partial observation beam paths with the optical axes 14, 16 on the side of the microscope main objective system 18 facing away from the object region 12. Moreover, the illumination device 34 contains a reflection stop 50 which is parallel to the optical axis 84 of the microscope main objective system 18, which is perpendicular to an optical axis of the illumination beam path 64 coaxial with the optical axis 90 of the collector lens system 54, and which is arranged at a minimal distance upstream of the deflection element 58 as seen in the illumination beam path 64 from the luminous plane 46.

The diagonals 91, parallel to the stereo base 82, of the luminous areas 44 of the light sources 38, 40 of the light source assembly 36 in the illumination device 34 are located on a straight line perpendicularly intersecting the optical axis 90. In contrast, the diagonal 91 of the luminous area 44 intersects the optical axis of the illumination beam path 64 perpendicularly. This arrangement of the luminous areas 44 of the light sources 38, 40 ensures that, firstly, the amount of light that can be guided in the illumination beam path to the object region 12 is maximized, and reflections of the illumination light which can reach into the stereoscopic partial observation beam paths 78, 80 are prevented from arising at optically effective surfaces of the microscope main objective system.

Figure 8:
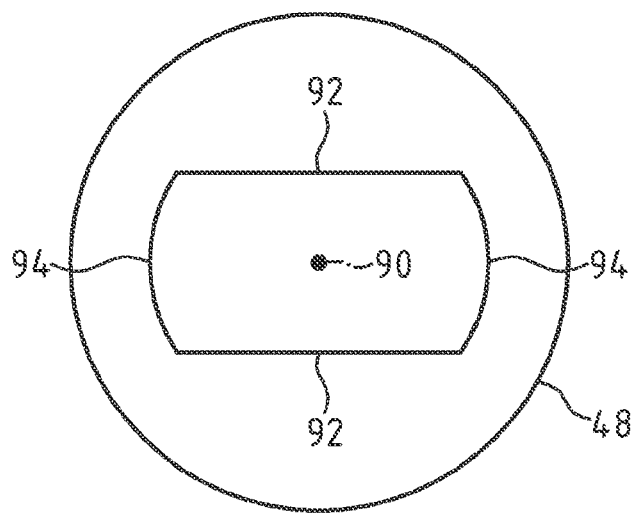
FIG. 8 shows a radiant field stop of the illumination device.

FIG. 8 shows the radiant field stop 48 of the illumination device 34. The stop opening of the radiant field stop 48 has a base side 92 parallel to the stereo base 82 of the stereoscopic partial observation beam paths in sectional planes of the microscope main objective system 18 perpendicular to the optical axis 84 and is laterally delimited by with respect to the optical axis of the illumination beam path 64 of the circular arcs 94 coinciding with the optical axis 90 of the collector lens system 54, the geometry of which maximizes the light yield in the luminous field generated on the object region 12.

Figure 9:
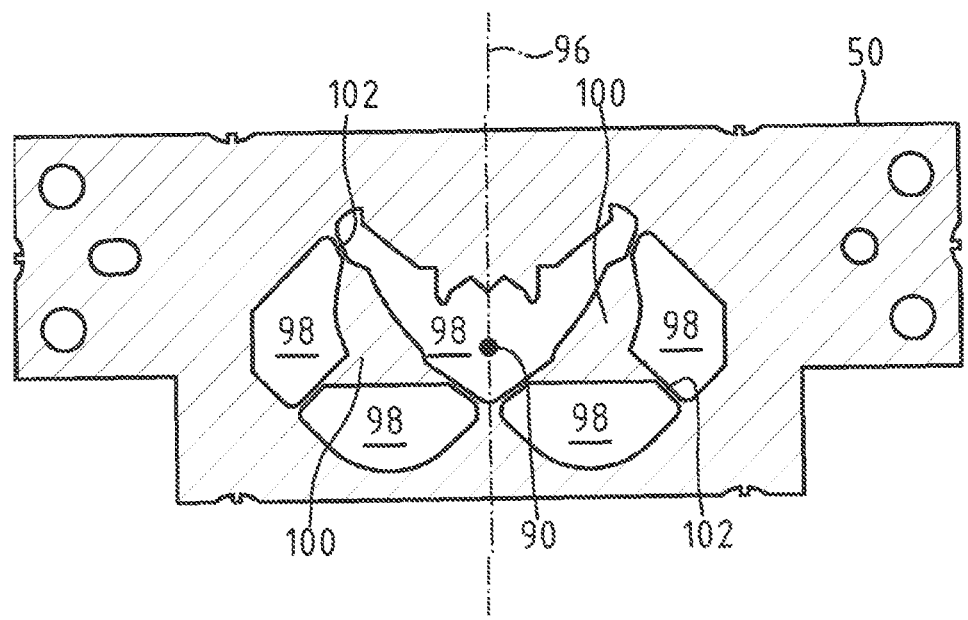
FIG. 9 shows a reflection stop of the illumination device.

FIG. 9 shows the reflection stop 50 for suppressing reflections of the illumination light at optically effective surfaces of the microscope main objective system 18 on a side facing away from the object region 12 and having the optical axis 90 of the collector lens system 54, which corresponds to an optical axis of the illumination beam path 64. The reflection stop 50 is made of a thin sheet metal, for example. In the illumination device 34, the reflection stop 50 is located in a portion of the imaging beam path of the luminous plane 46 in which the light rays of the illumination light converge, close to the luminous image plane 65. The reflection stop 50 is mirror-symmetrical with respect to an axis of symmetry 96 parallel to the optical axis 84 of the microscope main objective system 18. This axis of symmetry 96 perpendicularly intersects the optical axis of the illumination beam path 64, which is coaxial with the optical axis 90 of the collector lens system 54. The reflection stop 50 includes five separate light passage surfaces 98 which surround two opaque regions 100 which are held on webs 102.

On account of a small distance between the reflection stop 50 and the luminous image plane 65, the reflection stop 50 only has to mask the illumination light that is guided near the optical axis of the illumination beam path 64, which coincides with the optical axis 90 of the collector lens system 54, in order to avoid disturbing reflections of the illumination light at the microscope main objective system 18. The arrangement of the reflection stop 50 in the illumination beam path 64 ensures that it can be kept small and it is able to mask illumination light that has defined critical points of incidence on the optical interfaces of the microscope main objective system 18.

It should be observed that a reflection stop can in principle also be arranged close to the light source assembly 36 in the illumination beam path 64 in order to avoid the occurrence of disturbing reflection light in the stereoscopic partial observation beam paths 78, 80, although this then necessitates the acceptance of relatively large losses of illumination light in the case of the geometry and arrangement, described here, of the luminous areas 44 in the luminous plane 46. It should also be observed that, in order to avoid disturbing reflections of the illumination light, deflected to the microscope main objective system 18 with the mirror element 60, at the optically effective interfaces of the microscope main objective system 18, a further reflection stop can in each case be arranged upstream of the adjustable lens assemblies 22, 24 of the magnification system 20.

It should moreover be observed that the microscope main objective system 18 can in principle also be slightly tilted in order to avoid disturbing reflections of illumination light in the stereoscopic partial observation beam paths 78, 80, although this has a negative effect on the imaging quality of the surgical microscope 10.

Figure 10:
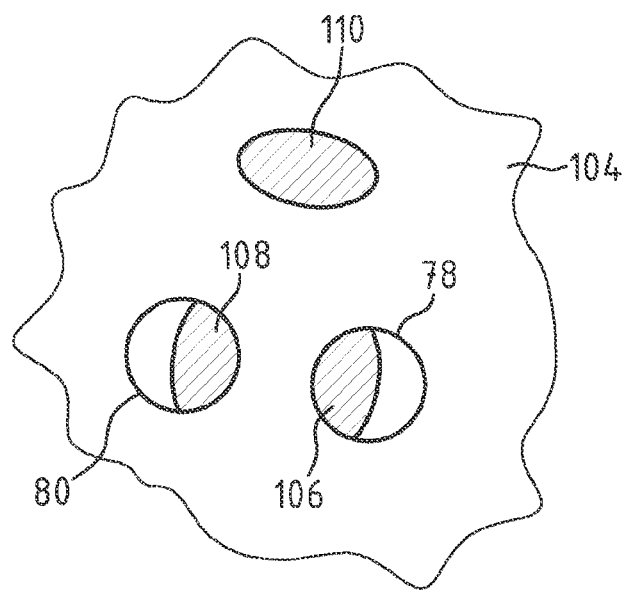
FIG. 10 shows luminous spots produced with the illumination de-vice on the fundus of a patient's eye.

FIG. 10 shows a partial view of the retina 104 of a patient's eye shown in FIG. 1, which is centered with respect to the optical axis 84 of the microscope main objective system 18 in the surgical microscope 10. The luminous spots 106, 108, which are generated here with the illumination device 34 of the surgical microscope 10 and which can be traced back to the light from the light sources 38, 40, overlap with the region of the retina 104 through which pencils of rays of the stereoscopic partial observation beam paths 78, 80 pass. With the luminous spot 110, which is caused by the light from the light source 42, they define the corners of a triangle.

A peculiarity of the surgical microscope 10 described above is that the illumination light from the luminous areas 44 of the light sources 38, 40 and 42 is available over the entire luminous field 61 in the object region 12. The illumination light of the light sources 38, 40 in the illumination device 34 of the surgical microscope 10 therefore makes it possible to generate red reflex illumination even in a patient's eye 11 which is off-centered in relation to the optical axis of the microscope main objective system 18 in the object region 12.

In conclusion, the following should be registered: A surgical microscope 10 contains an optical assembly 15 configured to image an object plane 32, which is arranged in an object region 12, into an image plane 30. The optical assembly 15 includes a microscope main objective system 18, through which a first stereoscopic partial beam path with a first optical axis 14 and a second stereoscopic partial beam path with a second optical axis 16 pass. In the surgical microscope 10 there is an illumination device 34 for illuminating the object region 12 with an illumination beam path 64, said illumination device containing a light source assembly 36 for providing illumination light in a luminous plane 46, having a radiant field stop 48 arranged at a distance from the luminous plane 46, and containing an illumination optical unit 52 configured to image the radiant field stop 48 in a radiant field stop plane on a side of the microscope main objective system 18 facing the object region 12 with a beam path passing through the microscope main objective system 18. The illumination optical unit 52 at least partially images a luminous object arranged in the luminous plane 46 in the illumination beam path 64 into at least one luminous image plane 65, 68 which is perpendicular to the optical axis of the micro-scope main objective system (18) and which is located in the microscope main objective system 18 or for the vertical distance z of which from the microscope main objective system 18 on the side facing the object region 12 or the side facing away from the object region 12, in relation to a focal length f of the microscope main objective system 18, the following applies: $z/f \leq 10\%$, typically $z/f \leq 5\%$, particularly typically $z/f \leq 2.5\%$.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

10 Surgical microscope
11 Patient's eye
12 Object region
14 Optical axis of a first stereoscopic partial observation beam path
16 Optical axis of a second stereoscopic partial observation beam path
15 Optical assembly
17 Surgical microscope main body
18 Microscope main objective system
20 Magnification system
22 First adjustable lens assembly of the magnification system
24 Second adjustable lens assembly of the magnification system
26 Binocular tube
28 Tube lens
30 Image plane
32 Object plane
34 Illumination device
35 Eyepiece lens
36 Light source assembly
38, 40, 42 Light sources
44 Luminous area
45 Centroid
46 Luminous plane
47 Point of intersection
48 Radiant field stop
50 Reflection stop
52 Illumination optical unit
54 Collector lens system
56 Converging lens system
58 Deflection element
60 Mirror element
61 Luminous field
62 Sectional plane
63 Luminous field plane
64 Illumination beam path
65, 65', 68 Luminous image plane
66 Light trap
70 Optical axis of the imaging beam path
72, 74, 76 Image
78 First stereoscopic partial observation beam path
80 Second stereoscopic partial observation beam path 82 Stereo base
84 Optical axis of the microscope main objective system
86 Normal
88 Center point
90 Optical axis of the collector lens system
91 Diagonal
92 Base
94 Circular arc
96 Axis of symmetry
98 Light passage surface
100 Opaque region
102 Web
104 Retina
106, 108 Luminous spot
110 Luminous spot

What is claimed is:

1. A surgical microscope, comprising:
an optical assembly configured to image an object plane into an image plane, the object plane being arranged in an object region, the optical assembly including a microscope main objective system, through which a first stereoscopic partial beam path with a first optical axis and a second stereoscopic partial beam path with a second optical axis pass; and
an illumination device configured to illuminate the object region with an illumination beam path, the illumination device including a light source assembly configured to provide illumination light into a luminous plane which generates an extensive luminous pattern in the luminous plane, the extensive luminous pattern including a first luminous area and a second luminous area arranged at a distance from the first luminous area, the first luminous area and the second luminous area being mirror-symmetrical in relation to an optical axis of the illumination optical unit, a radiant field stop arranged at a distance from the luminous plane, and an illumination optical unit configured to image the radiant field stop into a radiant field stop plane on a first side of the microscope main objective system facing the object region with a beam path passing through the microscope main objective system,
wherein the illumination optical unit at least partially images a luminous object arranged in the luminous plane in the illumination beam path into at least one luminous image plane, wherein the at least one luminous image plane is located (a) in the microscope main objective system, or (b) at a vertical distance z from the microscope main objective system on the first side of the microscope main objective system facing the object region or on a second side of the microscope main objective system facing away from the object region,
wherein f defines a focal length of the microscope main objective system,
wherein the following applies: $z/f \leq 10\%$, and
wherein the illumination optical unit images the luminous pattern as an extensive luminous pattern image into the at least one luminous image plane optically conjugate to the luminous plane.

2. The surgical microscope as claimed in claim 1, wherein the illumination optical unit images the luminous object arranged in the luminous plane with magnification.

3. The surgical microscope as claimed in claim 1, wherein the luminous image plane is perpendicular to an optical axis of the microscope main objective system.

4. The surgical microscope as claimed in claim 1, wherein the luminous pattern image is located at least in part on a straight line perpendicularly intersecting the first optical axis of a first stereoscopic partial observation beam path and the second optical axis of a second stereoscopic partial observation beam path in the at least one luminous image plane.

5. The surgical microscope as claimed in claim 4, wherein the first stereoscopic partial observation beam path at least partially passes through the luminous pattern image and/or the second stereoscopic partial observation beam path at least partially passes through the luminous pattern image.

6. The surgical microscope as claimed in claim 5, wherein the first optical axis of the first stereoscopic partial observation beam path passes through the luminous pattern image and/or the second optical axis of the second stereoscopic partial observation beam path passes through the luminous pattern image.

7. The surgical microscope as claimed in claim 4, further comprising a reflection stop configured to suppress illumination light reflections in at least one of the first and second stereoscopic partial beam paths on a side of an optically effective surface of the microscope main objective system facing away from the object region, the reflection stop being arranged in the illumination beam path on the second side of the microscope main objective system facing away from the object region, at a distance both from the luminous plane and from at least one sectional plane of the microscope main objective system optically conjugate to the luminous plane.

8. The surgical microscope as claimed in claim 7, wherein at least one of:
the reflection stop is arranged in a stop plane parallel to the optical axes of the first stereoscopic partial observation beam path and the second stereoscopic partial observation beam path,
the reflection stop has a mirror-symmetrical stop structure and comprises a plurality of light passage surfaces separated from one another by opaque regions, and
the reflection stop is arranged in a portion of the illumination beam path in which the illumination beam path is convergent or is divergent.

9. The surgical microscope as claimed in claim 1, wherein the illumination optical unit comprises a deflection element arranged on the second side of the microscope main objective system facing away from the object region, which serves to deflect illumination light provided with the illumination device to the object region, and which has a mirror surface which is parallel to a stereo base of the first stereoscopic partial beam path and the second stereoscopic partial beam path and in which a straight line coaxial with the stereo base runs.

10. The surgical microscope as claimed in claim 9, wherein the deflection element is formed as a beam splitter through which the first stereoscopic partial beam path and the second stereoscopic partial beam path pass.

11. The surgical microscope as claimed in claim 1, wherein the illumination device has a mirror element which is arranged on the second side of the microscope main objective system facing away from the object region, the mirror element being positioned at a distance from an optical axis of the microscope main objective system, and, for a deflection of illumination light to the object region, the mirror element has a mirror surface parallel to a stereo base of the first stereoscopic partial beam path and the second stereoscopic partial beam path, and/or
wherein the illumination optical unit at least partially images the luminous object arranged in the luminous plane in the illumination beam path into different luminous image planes, wherein each of the different luminous image planes is located (a) in the microscope main objective system, or (b) at the vertical distance z from the microscope main objective system on the first side of the microscope main objective system facing the object region or on the second side of the microscope main objective system facing away from the object region, wherein f defines the focal length of the microscope main objective system, and wherein the following applies: $z/f \leq 10\%$.

12. The surgical microscope as claimed in claim 1, wherein the illumination device further comprises a collector lens system with an optical axis and a converging lens system, and
wherein the radiant field stop is arranged between the luminous plane and the collector lens system.

13. The surgical microscope as claimed in claim 12, wherein the light source assembly comprises two light sources, each of the two light sources having a rectangular luminous area arranged in the luminous plane, the luminous areas having centroids which are spaced apart from one another and located on a straight line which perpendicularly intersects the optical axis of the collector lens system, and boundary sides running obliquely with respect to the straight line, or
wherein the light source assembly comprises the two light sources, each of the two light sources having a round luminous area arranged in the luminous plane, the luminous areas having centroids which are spaced apart from one another and located on a straight line which perpendicularly intersects the optical axis of the collector lens system, the boundary sides running orthogonally with respect to the straight line.

14. The surgical microscope as claimed in claim 13, wherein the light source assembly comprises a further light source with a rectangular or round luminous area arranged in the luminous plane,
wherein the further light source has a centroid arranged at a distance from the optical axis of the collector lens system, and
wherein the centroid is located on a straight line which perpendicularly intersects the optical axis and which is parallel to the luminous image plane conjugate to the luminous plane or to the optical axis of the microscope main objective system.

15. A surgical microscope, comprising:
an optical assembly configured to image an object plane into an image plane, the object plane being arranged in an object region, the optical assembly including a microscope main objective system, through which a first stereoscopic partial beam path with a first optical axis and a second stereoscopic partial beam path with a second optical axis pass; and
an illumination device configured to illuminate the object region with an illumination beam path, the illumination device including a light source assembly configured to provide illumination light into a luminous plane which generates an extensive luminous pattern in the luminous plane, the extensive luminous pattern including a first luminous area, a second luminous area, and a third luminous area, a radiant field stop arranged at a distance from the luminous plane, and an illumination optical unit configured to image the radiant field stop into a radiant field stop plane on a first side of the microscope main objective system facing the object region with a beam path passing through the microscope main objective system,
wherein the illumination optical unit at least partially images a luminous object arranged in the luminous plane in the illumination beam path into at least one luminous image plane, wherein the at least one luminous image plane is located (a) in the microscope main objective system, or (b) at a vertical distance z from the microscope main objective system on the first side of the microscope main objective system facing the object region or on a second side of the microscope main objective system facing away from the object region,
wherein f defines a focal length of the microscope main objective system,
wherein the following applies: $z/f \leq 10\%$,
wherein the illumination optical unit images the luminous pattern as an extensive luminous pattern image into the at least one luminous image plane optically conjugate to the luminous plane, and
wherein centroids of the first luminous area, the second luminous area, and the third luminous area in the luminous plane define an isosceles triangle with a height h perpendicularly intersecting a base c, the illumination optical unit imaging the base c of this triangle onto a straight line perpendicularly intersecting the optical axis of the first stereoscopic partial observation beam path and the optical axis of the second stereoscopic partial observation beam path in the luminous image plane such that an image of a point of intersection of the height h with the base c of the triangle is located on a center point of a distance line perpendicularly intersecting the first optical axis of the first stereoscopic partial observation beam path and the second optical axis of the second stereoscopic partial observation beam path in the luminous image plane.

16. The surgical microscope as claimed in claim 15, wherein the light source assembly is configured to set different luminous patterns.

17. The surgical microscope as claimed in claim 15, wherein the luminous pattern has at least one rectangular luminous area, at least one square luminous area, or at least one round luminous area.

18. A surgical microscope, comprising:
an optical assembly configured to image an object plane into an image plane, is the object plane being arranged in an object region, the optical assembly including a microscope main objective system, through which a first stereoscopic partial beam path with a first optical axis and a second stereoscopic partial beam path with a second optical axis pass; and
an illumination device configured to illuminate the object region with an illumination beam path, the illumination device including a light source assembly configured to provide illumination light into a luminous plane, a radiant field stop arranged at a distance from the luminous plane, and an illumination optical unit configured to image the radiant field stop into a radiant field stop plane on a side of the microscope main objective system facing the object region with a beam path passing through the microscope main objective system,
wherein the illumination optical unit at least partially images a luminous object arranged in the luminous plane in the illumination beam path into at least one luminous image plane located in the microscope main objective system or for a vertical distance z of which from the microscope main objective system on the side facing the object region or the side facing away from the object region, in relation to a focal length f of the microscope main objective system, the following applies: $z/f \leq 10\%$, wherein, to image the luminous plane, the illumination device comprises a collector lens system with an optical axis and a converging lens system, the radiant field stop being arranged between the luminous plane and the collector lens system, and wherein the light source assembly comprises two light sources, each of the two light sources having a rectangular luminous area arranged in the luminous plane, the luminous areas having centroids which are spaced apart from one another and located on a straight line which perpendicularly intersects the optical axis of the collector lens system, and boundary sides running obliquely with respect to this straight line, or wherein the light source assembly comprises the two light sources, each of the two light sources having a round luminous area arranged in the luminous plane, the luminous areas having centroids which are spaced apart from one another and located on a straight line which perpendicularly intersects the optical axis of the collector lens system, the boundary sides running orthogonally with respect to the straight line.

19. The surgical microscope as claimed in claim 18, wherein the luminous image plane is perpendicular to an optical axis of the microscope main objective system.

* * * * *